United States Patent
Ehwald et al.

(10) Patent No.: US 9,200,244 B2
(45) Date of Patent: Dec. 1, 2015

(54) METHOD FOR CULTURING PHOTOAUTOTROPHIC MICROORGANISMS FOR THE PRODUCTION OF BIOMASS

(71) Applicant: Celldeg GbR, Berlin (DE)

(72) Inventors: Rudolf Ehwald, Berlin (DE); Lars Bähr, Berlin (DE); Arne Wüstenberg, Berlin (DE); Joel Herve Soh, Berlin (DE)

(73) Assignee: Celldeg GbR, Berlin (DE)

( * ) Notice: Subject to any disclaimer, the term of this patent is extended or adjusted under 35 U.S.C. 154(b) by 4 days.

(21) Appl. No.: 14/358,045

(22) PCT Filed: Nov. 16, 2012

(86) PCT No.: PCT/EP2012/072909
§ 371 (c)(1),
(2) Date: May 14, 2014

(87) PCT Pub. No.: WO2013/072495
PCT Pub. Date: May 23, 2013

(65) Prior Publication Data
US 2014/0315280 A1    Oct. 23, 2014

(30) Foreign Application Priority Data
Nov. 17, 2011   (DE) .................. 10 2011 055 448

(51) Int. Cl.
*C12N 1/12*     (2006.01)
*C12N 1/04*     (2006.01)
*C12M 1/00*     (2006.01)
*C12M 1/12*     (2006.01)

(52) U.S. Cl.
CPC ............... *C12M 21/02* (2013.01); *C12M 23/06* (2013.01); *C12M 23/34* (2013.01); *C12M 25/02* (2013.01); *C12M 29/26* (2013.01); *C12M 31/08* (2013.01); *C12N 1/12* (2013.01)

(58) Field of Classification Search
USPC ............................................ 435/257.1, 260

IPC .......................... C12N 1/12,1/04; C12M 21/02
See application file for complete search history.

(56) References Cited

FOREIGN PATENT DOCUMENTS

| EP | 2258463 A1 | 12/2010 |
|---|---|---|
| WO | 2008055190 A2 | 5/2008 |

OTHER PUBLICATIONS

Pors et al. A Batch Culture Method for Microalgae and Cyanobacteria With CO2 Supply Through Polyethylene Membranes; Journal of Phycology, vol. 46 (2010) pp. 825-830.*
Ipal Gesellschaft für Patentverwertung Berlin mbH: "Photobioreactor", Nov. 14, 2012, XP002693727 Retrieved from the Internet: URL: http://www.ipal.de/sites/default/files/to_11033_ab_04092012.pdf the whole document.

* cited by examiner

*Primary Examiner* — Kagnew H Gebreyesus
*Assistant Examiner* — Paul Martin
(74) *Attorney, Agent, or Firm* — Michael Soderman (57) ABSTRACT

The invention relates to a method for cultivating photoautotrophic micro-organisms, comprising the following steps: provision of a photosynthesis layer, which contains a photosynthesis medium and photoautotrophic micro-organisms suspended therein, in a closed accommodation space having a gas-diffusion-inhibiting outer boundary, wherein the photosynthesis layer has an average thickness of no more than 10 mm; exposure of the photosynthesis layer without eddying or feeding through a gas in the photosynthesis medium while limiting the diffusive gas exchange of the accommodation space by the environment, wherein the supply of micro-organisms in the photosynthesis medium with hydrogen carbonate ions is maintained by storing hydrogen carbonate ions in the photosynthesis medium and/or providing a photosynthesis substrate in the form of carbon dioxide and hydrogen carbonate from a cell-free carbon storage medium outside the photosynthesis layer; and conducting a gas formed during photosynthesis out of the accommodation space.

10 Claims, 7 Drawing Sheets

METHOD FOR CULTURING PHOTOAUTOTROPHIC MICROORGANISMS FOR THE PRODUCTION OF BIOMASS

CROSS REFERENCE TO RELATED APPLICATIONS

This application is the U.S. national stage of International Application No. PCT/EP2012/072909 filed on Nov. 16, 2012, and claims the benefit thereof. The international application claims the benefit of German Application DE 102011055448.3 filed on Nov. 17, 2011; all applications are incorporated by reference herein in their entirety.

BACKGROUND

Currently, the range of commercial and industrial products obtainable from photoautotrophic microorganisms is broadened with the help of genetic engineering. In the following, the term photoautotrophic microorganisms will be used for cyanobacteria and eukaryotic micro-algae of different divisions, mainly rhodophyta, heterokonta, euglenophyta and chlorophyta, with a size of the cells or cell aggregates below 20 µm.

The genomes of the cyanobacterium *Sychenocystis* sp. PCC 6803, the green alga *Chlamydomonas reinhardtii* and other biotechnologically important photoautotrophic microorganisms have been decrypted, and transgenic strains with the potential for producing different biotechnologically relevant organic substances by photosynthesis became available. The main source of carbon in photo-bioreactors is carbon dioxide supplied to cell suspensions of these microorganisms by introducing air or a carbon dioxide-air mixture into the cell suspension. The avoidance of carbon dioxide depletion zones and light deficiency in photo-bioreactors is technically difficult when cyanobacteria and micro-algae occur in a high biomass concentration. The use of high concentrations of potassium or sodium bicarbonate is a well-known way of increasing the pH and promoting the growth of the culture of the alkaliphilic large-cell organism *Spirulina plantenis* in illuminated open tanks exchanging carbon dioxide with the atmosphere.

From stoichiometric reasons a bicarbonate medium used as the sole carbon source cannot contain enough stock for the growth up to high biomass concentrations, unless its carbon concentration is more than 200 mmol $L^{-1}$. It is, however, known that many cultures die off in media with much lower bicarbonate concentrations. The growth of shaken cultures of photoautotrophic microorganisms can be promoted by a membrane-bordered carbon reservoir (DE 2009/10 2008 029 169). The latter consists of a concentrated aqueous buffer solution of bicarbonate and carbonate ions in a bag made of a thin polyethylene film. Carbon dioxide is discharged with controlled rate to the cell suspension through the gas-permeable membrane of this bag.

SUMMARY

A process for the cultivation of photoautotrophic microorganisms is proposed. This process comprises
providing a photosynthesis layer (2) with a mean thickness of not more than 10 mm that contains a photosynthesis medium and photoautotrophic microorganisms suspended therein and is located within a closed space with an outer border (1) acting as barrier for gas diffusion, exposure of the photosynthesis layer (2) to the light without whirling a gas within the photosynthesis medium or piping a gas through this medium
maintaining a bicarbonate concentration of at least 10 mM in the photosynthesis medium by application of a photosynthesis medium with an initial concentration above 50 mM, preferably above 200 mM, and/or the continuous delivery of a carbon substrate for photosynthesis chosen from the group comprising carbon dioxide and bicarbonate ions from a cell-free carbon storage medium (4) that is located outside of the photosynthesis medium by diffusion through a membrane that is permeable to the photosynthesis substrate and
convective channeling away of the gas volume formed at photosynthesis through an appliance for the gas outlet.

DETAILED DESCRIPTION

To improve the carbon supply to photoautotrophic microorganisms in photosynthesis layers of limited thickness, and to combine good substrate distribution with an optimal light distribution for the production of oxygen, biomass or organic material by the photoautotrophic microorganisms, a method is proposed according to various embodiments described in claims 1 to 10.

In photosynthesis layers of small thickness photosynthesis is limited by insufficient penetration of light only at high cell densities. Photosynthetic layers in the sense used here are liquid or liquid compartments of limited thickness, which are bordered by a transparent solid and are in direct contact with a gas phase. The arrangement of suspensions of photoautotrophic microorganisms in layers of small thickness favors a high rate of photosynthesis referred to the suspension volume. According to the invention, stirring and intermingling of the cells by passing a gas containing carbon dioxide through the thin photosynthesis layer is disclaimed. In the proposed method, a photosynthesis layer in a photo-bioreactor with an average layer thickness of about 10 mm or less is exposed to sunlight or the photosynthetic active light radiation of a suitable artificial light source, while the cells of the photoautotrophic microorganism in the photosynthesis layer are suspended in a mineral photosynthesis medium with a bicarbonate concentration of preferably more than 10 mM. The proposed method disclaims the passing of a gas through the suspension of the photoautotrophic microorganisms or through the photo-bioreactor, this way enabling and facilitating the use of very thin photosynthesis layers, where the usual method for stirring the cells in the light gradient and distribution of the dissolved carbon dioxide by an ascending gas is rendered difficult. Instead, the carbon substrate is included as a stock either within the photosynthesis medium or introduced into the latter by diffusion through a transparent membrane. The creation of substrate deficient zones with high pH in the cell suspension of the photoautotrophic microorganisms is prevented or retarded by the maintenance of a bicarbonate concentration of preferably at least 10 mM. This is realized either by a high initial bicarbonate concentration in the culture medium itself or by the use of a separate cell-free carbon stock medium. The carbon stock medium is a fluid compartment delivering bicarbonate ions and/or carbon dioxide to the photosynthesis medium in the way of permeation of these molecules through a substrate-permeable and translucent membrane that is permeable to a carbon substrate.

Figure 1:
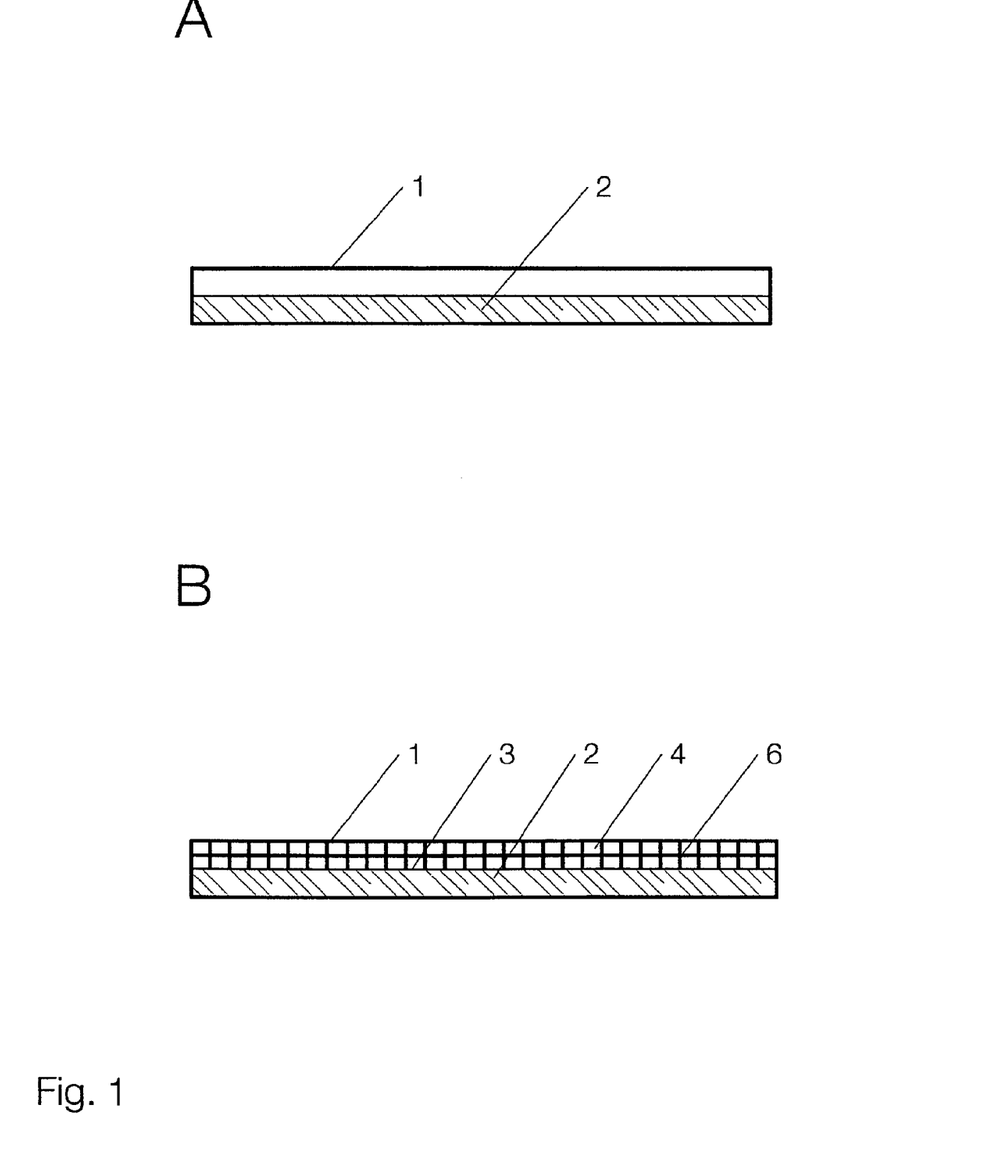

FIG. 1 schematically describes a photo-bioreactor with the components essential for the process. The maintenance of a concentration of bicarbonate ions in a photosynthesis medium of preferably about 10 mM prevents the occurrence of diffusion-based substrate depletion zones in the unstirred photosynthesis layer or in a photosynthesis layer that is kept at laminar flow. This enables high rates of photosynthesis at high cell densities without whirling a carbon dioxide-containing gas into the cell-containing suspension. This is an advantage, since generating turbulent flow by continuous gas injection is energy-consuming and can result in steady shear stress acting on the cultured microorganisms that shortens the lifetime of the cells and might cause a non-desired development of foam, the suppression of which requires additional technical measures and costs.

In the present art the broad use of bicarbonate as the sole carbon source for photoautotrophic microorganisms in closed photo-bioreactors has been disclaimed since, as a rule, the concentrations of sodium or potassium bicarbonate which are required for this purpose are considered to be toxic. Unpublished results of the present inventors have, however, shown that the break down found in cultures of a biotechnologically important phototrophic microorganism, the freshwater cyanobacterium *Synechocystis* sp. PCC 6803, in media containing 30 to 50 mM sodium or potassium bicarbonate was not due to the toxicity of the bicarbonate and carbonate ions. Instead, the photosynthetic consumption of bicarbonate applied in these concentrations resulted in a rapid and strong increase of the pH to a toxic value of about 11. The rapid rise in pH combined with the cells' dying off happened only after reaching a critical cell density. Surprisingly, the above organism showed a stable growth rate of about one per day at a biomass concentrations of 0.5 to 1 g dry weight per liter when it was exposed to the light in a medium containing potassium carbonate or sodium bicarbonate in concentrations of 200 or 300 mM. The advantage of a photosynthesis medium with such a high concentration of bicarbonate ions consists in its high buffer capacity, which delays the metabolically induced increase in the medium pH value. In such a medium extremely high pH values that exceed the tolerance range of photoautotrophic microorganism will not be reached, since photosynthesis becomes severely reduced by light limitation due to the high cell density before the utilization of bicarbonate ions could increase the pH to the toxic level. Doubtless, besides *Synechocystis* sp. PCC 6803, there are numerous other phototrophic microorganisms which tolerate photosynthesis media containing soluble bicarbonate like potassium bicarbonate, sodium bicarbonate and magnesium bicarbonate in high concentration, if the toxic increase in pH can be prevented. It is beneficial for the process when the cultivated photoautotrophic microorganisms are alkali-tolerant and osmo-tolerant thus enabling the application of initial concentrations of bicarbonate in the photosynthesis medium above 200 mM or by the maintenance of a bicarbonate concentration above 50 mM with the help of a carbon stock medium. This enables efficient carbon substrate provision to relatively thick photosynthesis layers and prevents strong metabolically mediated pH gradients. However, the diffusive allocation of bicarbonate within photosynthesis layers of a thickness below 2 mm enables substrate saturation even at moderate bicarbonate concentrations of at least 10, preferably 20 mM, and especially preferably of 50 mM; which are maintained by delivery from a separate cell free carbon stock medium. Hence, the claimed process is applicable also to such phototrophic microorganisms, which are neither osmo-tolerant nor alkali-tolerant.

The proposed process involves the proved possibility of preventing a metabolically mediated pH increase only by application of a photosynthesis medium with an initial concentration above 50 mM, preferentially above 200 mM. This way it may be prevented that during a culture period the mean concentration of bicarbonate falls below 10 mM due to carbon dioxide consumption, thus forming zones of substrate deficiency and high pH.

Alternatively, the proposed process involves the possibility to use an additional carbon stock medium, from which bicarbonate and/or carbon dioxide is delivered to the photosynthesis layer. Delivery of bicarbonate by diffusion through a light transparent membrane enables the maintenance of a mean bicarbonate and/or carbon dioxide concentration in the photosynthesis medium above 10 mM and prevents or retards the formation of alkaline substrate deficiency zones. According to one or several embodiments of the proposed invention it is possible to use a light transparent and cell free carbon stock medium to increase the amount of stored carbon and to distribute light within the photo-bioreactor.

Hence, at the proposed process the release of oxygen is coupled stoichiometrically to the utilization of carbon dioxide or bicarbonate ions that are stored in the carbon stock medium and/or the photosynthesis medium.

A cell free carbon stock medium can be set into diffusive exchange with the photosynthesis medium through a hydrophilic porous membrane, for example a dialysis membrane consisting of viscose or regenerated cellulose or a nylon micro-filter membrane. In this case the carbon stock medium contains all components of the photosynthesis medium due to the diffusion of all ions through the hydrophilic porous membrane. The buffering capacity and the carbon storage capacity are increased by the additional volume of the cell free carbon stock medium. Preferably at this embodiment of the proposed process a mineral medium is used, which is supplied with potassium and/or sodium and/or magnesium bicarbonate. In order to ensure a high buffering capacity and to supply a sufficient amount of the carbon substrate, the initial concentration of the mentioned inorganic carbon compounds amounts preferably to at least 200 mM. Preferably, in this embodiment of the process the photosynthesis layer comprises a suspension of a photoautotrophic microorganism like *Synechocystis* sp. PCC 6803, which tolerates high or very high concentrations of potassium and sodium bicarbonate and pH values between 9 and 10.5. A tolerance to very high concentrations of potassium and/or sodium bicarbonate can be generally expected for marine photoautotrophic microorganisms or for those microorganisms which have been isolated from soda or natron lakes. As own results have shown, such a tolerance is also a feature of certain euryhaline cyanobacteria or micro-algae considered as fresh water organisms. The application of bicarbonate ions, in concentrations as high as possible, has the advantage—besides a high volume-based storage capacity for inorganic carbon—that the growth of the photoautotrophic microorganism proceeds on a selective medium with high osmotic pressure, high ion strength, and, if indicated, of high pH. This strongly reduces the probability of contamination with microbes from the air.

In a further embodiment of the process a hydrophobic membrane that is impermeable for water and water soluble materials but permeable for gases and light is applied for delivering of the carbon substrate to the photosynthesis layer. In this case the carbon storage medium used in the combination with such membrane is a liquid, which contains carbon dioxide as a dissolved gas or carbon dioxide bound to a solute chemically in a reversible manner. Liquids suitable as carbon storage medium are those, in which carbon dioxide is dissolved in a high concentration or those which have a high absorption coefficient for carbon dioxide. Thus it is possible to obtain a high concentration of carbon dioxide at a relatively low carbon dioxide partial pressure. Liquids suitable as such a carbon storage medium are for example Fluor Solvent (propylene carbonate) provided by the Fluor Daniel company or Selexo® (a mixture of dimethyl ethers and polyethylene glycol) provided by the company Union Carbide. As is well known, the mentioned and further suitable organic liquids like ethylene carbonate and further cyclic alkylene carbonates are applied for removal of carbon dioxide from gases. In these liquids the carbon dioxide partial pressure is approximately proportional to the carbon concentration. The cell-free carbon dioxide storage medium may contain carbon dioxide for delivery to the photosynthesis layer through a hydrophobic gas-permeable membrane in dissolved state or the chemically reversibly bound state. Examples for the storage of carbon dioxide by reversible binding to a dissolved material are aqueous solutions of bicarbonate and carbonate of inorganic or organic bases, for example the tertiary amines or the potassium and/or sodium ions. Further examples are aqueous solutions of carbamate ions of the primary or secondary amines. These solutions have also a carbon dioxide partial pressure that is suitable for the delivery of carbon dioxide to the photosynthesis medium. As is well known, at the washing of combustion-off gases, carbon dioxide is bound reversibly to solutions of different alkanol amines in the form of carbamate ions.

When hydrophobic gas-permeable membranes are used for the delivery of carbon dioxide to the cell suspension in a photosynthesis layer, the cells of the photoautotrophic microorganism are not directly in contact with the carbon storage medium. Therefore, highly concentrated solutions and toxic liquids with high carbon storage capacity can be applied, whereat the ions of the photosynthesis medium do not exchange with the carbon storage medium and must not be added to the latter. It is possible to adapt the carbon dioxide delivery into the photosynthesis medium to the photosynthesis rate by the choice of a membrane with certain gas permeability or the choice of the carbon dioxide partial pressure of the liquid carbon storage medium. There is a broad range for adjusting the gas permeability by the thickness of the membrane. As is well known, thin translucent films consisting of polyethylene or polypropylene have a high permeability for oxygen and carbon dioxide and are useful for package of fruits and vegetables or other moist materials due to their low permeability to water vapor. They are broadly available and have excellent processing properties. According to one or several embodiments of the process it can be beneficial to apply a carbon storage medium that is under positive pressure.

According to several embodiments of the proposed process the latter may be carried out in such a way that the photosynthesis layer is separated from a first carbon storage compartment by a first membrane being porous and permeable to water and dissolved ions. The first carbon storage medium delivering bicarbonate to the photosynthesis layer may be in further exchange with a second carbon storage medium across a hydrophobic gas-permeable membrane delivering carbon dioxide to the first carbon storage medium in order to regenerate the consumed bicarbonate ions.

According to a further embodiment, one carbon substrate, bicarbonate, is supplied to one face of photosynthesis layer by diffusion from a carbon storage medium resembling the photosynthesis medium and another one, carbon dioxide, is supplied to the other face from a second carbon storage medium by way of diffusion across a hydrophobic gas-permeable membrane.

The described combination of a first cell-free carbon storage medium resembling the photosynthesis medium that increases the buffering capacity of the photosynthesis medium, with a further carbon storage medium with a high concentration of bound carbon dioxide is especially beneficial. It creates a high carbon storage capacity in the photobioreactor and enables the sampling/harvesting of cell-free products of photosynthesis by putting the first carbon storage medium on flow. Putting on flow of the suspension of the photoautotrophic microorganisms within the photosynthesis layer or of a first carbon storage medium separated from the cell suspension by a porous membrane enables the harvesting of biomass on the one hand and the harvesting of diffusible products of photosynthesis on the other hand.

According to one or several embodiments of the proposed process the increase in the pH value occurring due the consumption of bicarbonate ions or of carbon dioxide in the photosynthesis medium is controlled by the addition of an acid to the carbon storage medium. This offers the benefit that photoautotrophic microorganisms of low alkali tolerance can be applied. A further benefit consists in the almost complete utilization of the inorganic carbon, when the substrate concentration in the photosynthesis medium is decreasing at increasing pH. As is well know, this is the case in the aqueous solutions of carbamate ions or bicarbonate/carbonate buffers.

According to one or more embodiments of the process, it is ensured by the design of the gas discharge and the control of the carbon dioxide partial pressure in the photobioreactor that the gas volume leaving the photobioreactor is largely determined by the volume of the photosynthetically produced oxygen. For example this offers the advantage that the stock of the photosynthesis substrate in the photobioreactor is retained longer than it would be the case without strict limitation of the diffusive carbon dioxide waste. For example one can design the gas outlet in order to control the diffusion of carbon dioxide out of the photobioreactor in such a way that the gas leaves the photobioreactor by viscous flow mainly. To assure this, the outer wall can be realized for example by a largely gas tight material containing macroscopic pores with a small pore diameter and a small overall pore area. For this purpose the upper part of the outer border of the photobioreactor can be realized by a transparent acryl glass or polycarbonate board, wherein isolated pores with a diameter of 50 μm have been introduced by means of laser drilling. A low total area of these pores limits diffusion and prevents complete pressure equilibration leaving a small excess pressure in the photobioreactor by which the gas volume synthesized photosynthetically is convectively deduced. A further way to prevent diffusive loss of carbon dioxide consists in the conduction of the deduced gas by the help of a streaming channel, preferably through a tube or pipe into a liquid, wherein it rises to the surface in the form of bubbles. Alternatively, it is possible to deduce the gas on a convective path in a narrow capillary of tubing of to the outer atmosphere, adjusting the length and width of the convective path in such dimensions that the convective velocity is above the permeability coefficient of carbon dioxide in the convective path according to the laws of Fick and Hagen-Poiseuille. Diffusive release of carbon dioxide can be almost completely prevented by a gastight outer border with a convective gas outlet.

To reduce flow mediated carbon dioxide loss, it is beneficial to adjust the concentration ratios in the carbon storage compartment in such a manner that the carbon dioxide partial pressure in the gas phase of the photobioreactor is below 20 kPa. This way it is ensured that the volume fraction of carbon dioxide in the inner gas space of the photobioreactor is below that of oxygen. In this case the molar amount of carbon bound photo-synthetically is higher than that released with the volume flux of the gas to the atmosphere.

Delivery of the carbon substrate to the photosynthesis medium from a light transparent carbon storage medium brings about the advantage, that the carbon storage media can be arranged in the photobioreactor in such a manner, that they become effective light conductors and distribute the sun light or the light of an artificial source evenly to the area of the photosynthesis layer. It is possible in this connection to use the refraction of the light at the interfaces between the liquid and the membranes as well as additional reflectors induced in the inclusion space for an optima distribution of the light in the depth of the inclusion space.

In an exemplary embodiment, the proposed photobioreactor for the cultivation of photoautotrophic microorganisms comprises a closed inclusion space with an at least partly light-transparent outer border, which inhibits gas diffusion and enables the convective outlet of the gas volume produced by photosynthesis. The inclusion space contains at least a first compartment serving for the building of a photosynthesis layer containing a suspension of the photoautotrophic microorganisms in the photosynthesis medium, when the photobioreactor is in use. The mean maximal thickness of the photosynthesis layer is typically less than 10 mm. Each first compartment is separated by a translucent membrane being permeable for bicarbonate and/or carbon dioxide from a least one second compartment serving for the inclusion of the cell-free carbon storage medium (4). The second compartment can be separated from the first compartment that is foreseen to take up the suspension of the photoautotrophic microorganisms by a flexible hydrophilic and porous membrane. This membrane can be for example a translucent hydrophilic dialysis—or microfilter membrane made from Nylon®, regenerated cellulose, a cellulose derivative or the like, which is impermeable for the cells but permeable for water and the low-molecular-weight materials dissolved in water. There is a broad choice of such membranes for the use in ultrafiltration and dialysis. This embodiment of the photobioreactor enables the already described embodiment of the proposed process, where all low-molecular weight materials are exchanging between the photosynthesis layer and the photosynthesis medium.

According to a further embodiment, the second compartment for the inclusion of the carbon storage medium is separated from the first compartment containing the photosynthesis layer by a hydrophobic membrane which is impermeable to non-volatile water-soluble materials but permeable to carbon dioxide and other gases. For example, thin and/or microporous membranes made from polyolefin's like polyethylene, polypropylene or similar hydrophobic polymers are suitable. The advantage of this embodiment of the proposed photobioreactor consists in the consequence that the carbon storage medium is exchanging with the photosynthesis medium through the gaseous phase within the membrane. Therefore, liquids with very high substrate storage capacity that are toxic in direct contact with photoautotrophic microorganisms, for example a 3 mol $L^{-1}$ potassium bicarbonate buffer, can be used as carbon storage medium. This embodiment of the photobioreactor is also applicable for photoautotrophic organisms which are intolerant or weekly tolerant to high salt concentrations and pH values. By the choice of the thickness or porosity of the gas-permeable membrane it is possible to adjust the rate by which carbon dioxide enters the photosynthesis layer. It is possible to fill a fluid into the second compartment which contains carbon dioxide, for example pure carbon dioxide or a gas mixture or an organic fluid with a high absorption coefficient for carbon dioxide wherein carbon dioxide is enriched or which is saturated with carbon dioxide, or the aqueous solution of a material that is binding carbon dioxide reversibly. Further details of these embodiments can be learned from the description of the process.

According to a further embodiment, a compartment for the inclusion of carbon storage medium that is bordered by a hydrophobic gas-permeable membrane is combined with a further compartment that is separated from the photosynthesis medium by a hydrophilic porous membrane. Various alternatives of this combination are presented in FIG. 3 and FIG. 6. The hydrophobic gas-permeable membrane either separates the photosynthesis layer from a compartment foreseen for the inclusion of the carbon storage medium, or it separates two compartments foreseen for the inclusion of the different carbon storage media. The last mentioned embodiment enables the compensation of the carbon loss of the first carbon storage medium, from which bicarbonate was removed by diffusion into the photosynthesis layer, by the entrance of carbon dioxide through the hydrophobic gas-permeable membrane. This combination of two compartments containing different carbon storage media enables a high buffering capacity due to the bicarbonate storage medium (second storage medium) and large storage capacity for inorganic carbon by the carbon storage medium delivering carbon dioxide (first storage medium). The second cell-free carbon storage medium, which is in exchange with the photosynthesis layer across the hydrophilic porous membrane, enables the separation of the soluble products of photosynthesis from the cells and improves the diffusive substrate distribution within an unstirred photosynthesis layer. Further advantages of this embodiment can be learned from the description of the process.

The use of membrane borders enables the upright arrangement of one or more photosynthesis layer in different geometric embodiments, for example in the form of parallel or concentric photosynthesis layers separated by one or more carbon storage media. This is beneficial, as the light inclined from above or from the lateral face can be led deeply into the space of the photobioreactor and will be distributed by dispersion, reflection and diffraction to the area of the upright photosynthesis layers. This way it is possible to obtain high rates of photosynthesis referred to the volume of the photobioreactor with low technical coast.

In a cylindrical photobioreactor the upright photosynthesis layers can be situated in the gaps between several neighboring membrane tubing's filled with the carbon storage medium. In this embodiment, the fraction of the photosynthesis layers in the cross sectional area of the photobioreactor is only 25 to 30%. A higher volume portion of the photosynthesis layers in the photobioreactor can be reached in embodiments with upright bifacial layers bordered by membranes with a parallel, concentric or spiral arrangement as can be learned from FIGS. 3 and 6.

Figure 3:
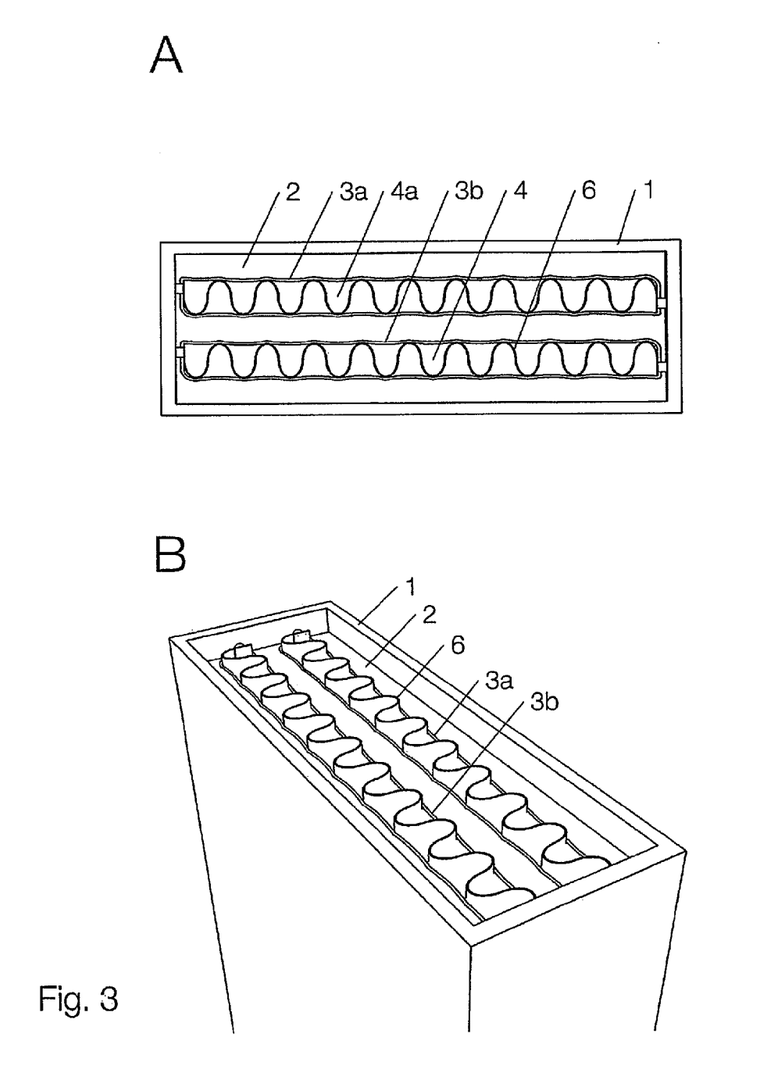
FIG. 3 the scheme of a photobioreactor with three photosynthesis layers, which are arranged upright and bordered by membranes, FIG. 4 a container for the carbohydrate storage medium which has been produced by the conglutination of two polypropylene membranes, whereat the membranes are strained by excess pressure, FIG. 5 the perspective of a meandering flow channel between two heat-sealed or clotted membranes.

According to a further embodiment of the photobioreactor the flexible membranes separating the photosynthesis layer from the cell-free medium which are transparent to light and permeable to the substrate are inserted in the shape of one or more bags with lateral extension, whereby the thickness of the layers of the cell-free medium and/or of the photosynthesis layer is fixed by spacers as envisaged in the FIGS. 1B and 3. Solid structures, which can limit the extension of a liquid layer between two flexible membranes, for instance grids, nettings, profile sheets and the like are suitable as spacer.

Especially beneficial spacers are formed in the shape of a profile sheet with a compressible wrinkle-like or wave-like profile. When such a profile sheet is introduced in an adapted profile sheet in the elastically compressed state, the lateral tension on the flexible membrane created hereby prevents its transverse extension thus creating flat compartments that are vertically or horizontally orientated. A schematic presentation of the use of a profile sheet within a bag shaped membrane can be learned from FIG. 3. When the profile sheet consists of light transparent or light reflecting material like acryl glass or stainless steal, it can contribute to the improvement of the light distribution to the photosynthesis layer. When the orientation of the wrinkles is horizontal, the cell sedimentation is restricted. Additionally the pleated profile can be used for the arrangement of parallel, horizontal or vertical flow channels in one or more membrane-bordered photosynthesis layer.

According to a further beneficial embodiment, the thickness of the photosynthesis layer or a layer of the carbohydrate storage medium is restricted by connections between two opposed membranes that are strip-shaped or point-shaped. This is envisaged schematically by the FIGS. 4 and 5. The advantage of this embodiment consists inter alias in low cost. Little material is required for establishing of a membrane bordered photosynthesis layer in such a way. In this connection the strip-shaped connection between the membrane areas can be preferably arranged such that a meandering flow channel is formed on the membrane area. This enables the continuous or discontinuous introduction of a diluted suspension into the illuminated photosynthesis layer or the sampling of biomass from the photosynthesis layer. Also the supply of the storage medium and the separation of the photosynthesis products from the cells are possible this way. Using a horizontal position of the channels in this embodiment limits the sedimentation of the cells. In these channels the carbon storage medium can flow continuously past the photosynthesis layer, whereby the permeable products of photosynthesis are enriched in the photosynthesis medium. The suspension of the photoautotrophic cells can be moved along the flow channel between the membrane connections, in order to harvest the formed biomass.

Figure 2:
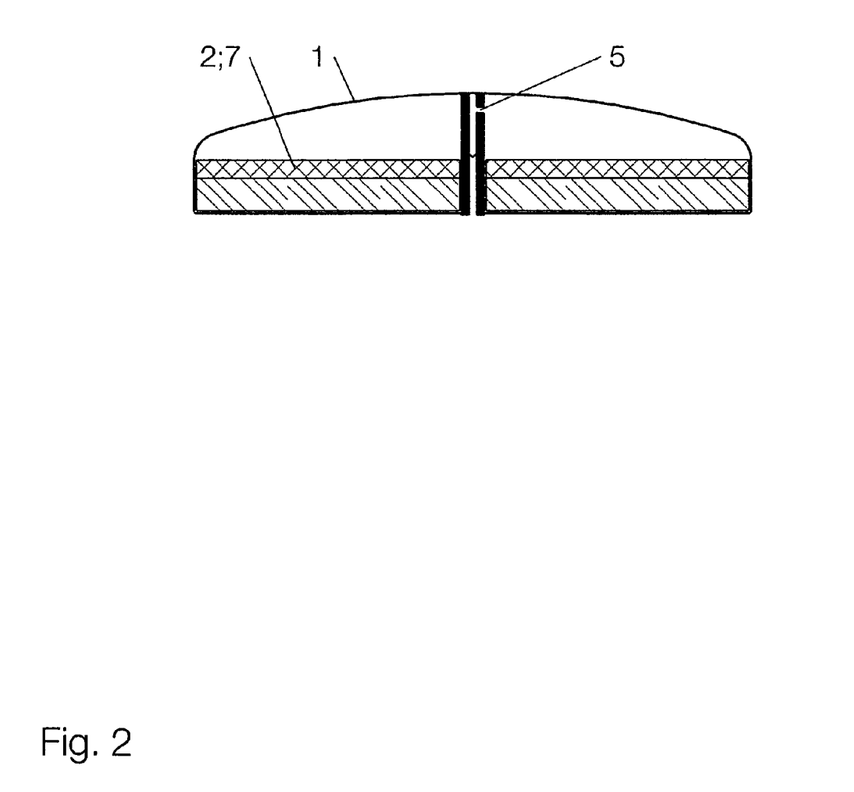
FIG. 2 the cross section of a photobioreactor with flexible outer border and a horizontally orientated photosynthesis layer.

According to a further embodiment shown schematically in FIG. 2, which is simply achievable and robust, only one horizontal photosynthesis layer and one gas space above this layer are included within the outer borders of the photobioreactor. The outer border, for example a translucent plastic film has the same basal area as the photosynthesis layer. The advantage of this embodiment consists in the fact that the photobioreactor can be illuminated when flowing on water as shown schematically in the figure. In this embodiment the gas outlet channel can be designed in a diffusion restricting manner as a tube with an outlet below the water table.

According to a further embodiment the photobioreactor with upright photosynthesis layer exhibits a pumping device preventing the sedimentation of the cells. This device keeps the suspension in movement by oscillating or circulating flow. Preferably several photosynthesis layers arranged upright in parallel are connected hydraulically are connected with one pumping device.

According to a further embodiment, the proposed photosynthesis layer is held within a matrix with partially open pores situated in the first compartment, this matrix developing a three-phase-system consisting of a light-transparent solid, a fine-dispersed gas phase and an aqueous liquid. When this matrix absorbs a suspension of the photoautotrophic microorganisms, a photosynthesis layer is formed, wherein the photoautotrophic microorganisms are surrounded by a fine dispersed gaseous phase and a fine dispersed liquid phase. The light-transparent and light-dispersing three phase system enables the diffusion of carbon dioxide over the gaseous phase and enables the diffusion of bicarbonate ions and of other water-soluble material in the liquid phase. Coincidentally the depth of light entrance into the photosynthesis layer is increased. An exemplary embodiment of the three phase system consists of an elastic and transparent foam material, whose pores are saturated partly by the photosynthesis medium and partly with air. It has been found that sheets made from different elastomers like latex and polyurethane are especially suitable. Very well suitable for establishing of the photosynthesis layer are sheets consisting of an open-pored light transparent and hydrophilic polyurethane foam. The use of such a sheet in the photosynthesis layer is shown in a horizontal position in FIG. 2 and in an upright position in FIG. 6. When a suspension of the photoautotrophic microorganisms is absorbed in these sheets, a three phase system with a fine dispersed gas phase is establishing by the inclusion of gas from the outside or by its formation by photosynthesis. The thickness of the photosynthesis layer can be controlled by the thickness of the foam sheet. The photoautotrophic microorganisms are absorbed within the capillary spaces. In different embodiments of the proposed photobioreactor high biomass concentrations have been reached by photosynthesis in a photosynthesis layer made from this material. The elasticity and mechanic toughness of the mentioned material enables beneficial processes of biomass harvesting and the supply of fresh medium by pressure application. This can be realized for instance by the help of a mechanic press or drum or by pressuring the translucent membranes hydraulically by means of a carbon storage medium. The supply of the photosynthesis layer with oxygen in a dark phase is possible without separate aeration, since the fine disperse gas phase stores oxygen formed during the light phase. In this embodiment it is possible to apply photosynthesis layers, which are separated by a gas-permeable membrane from a carbon storage medium delivering carbon dioxide across these membranes. Hereby the stock of oxygen for a dark phase is increased. According to an embodiment, the photobioreactor contains an elastic foam sheet in the first compartment and devices for forcing off the suspension of the photoautotrophic microorganisms from this sheet and for deducing this suspension out of the photobioreactor.

According to the invention a process for the cultivation of photoautotrophic microorganisms is provided in a photobioreactor with restricted diffusive gas exchange with the surroundings. The process comprises providing a photosynthesis layer containing a photosynthesis medium with photoautotrophic microorganisms suspended therein, whereby the photosynthesis medium contains bicarbonate in a concentration above 20 mM. Exposure to the light of the photoautotrophic microorganisms is carried out without swirling the photosynthesis medium and without piping a gas through this medium. According to an embodiment at least one substrate of photosynthesis chosen form a group comprising carbon dioxide and bicarbonate is provided to the photosynthesis layer from a carbon storage medium across a membrane that is transparent to light and permeable to the photosynthesis substrate.

BRIEF DESCRIPTION OF THE DRAWINGS

In the following beneficial embodiments are described and depicted in figures. Depicted are by FIG. 1 two photobioreactors with the essential components of the process in cross section.

DETAILED DESCRIPTION OF THE PREFERRED EMBODIMENT

FIG. 1 presents essential components of a photobioreactor for the execution of the proposed process in two embodiments. FIG. 1A: the photobioreactor has translucent outer border 1 restricting gas diffusion. The gas outlet appliance is not shown. The photosynthesis layer 2 is arranged horizontally and presented as cross section at right angle to the basal area. It can be exposed to the light from above. On top of the photosynthesis layer there is a gaseous phase. FIG. 1B: a photobioreactor with an upright photosynthesis layer is presented as cross section parallel to the basal area. The photosynthesis layer is enclosed in a thin bag of the substrate permeable membrane 3. The thickness of the bag is controlled by a spacer 6; realized in kind of a plastic grid. The bag is situated within in the liquid carbon-storage medium. In the upper part of the photobioreactor there is a gas space on top of the photosynthesis layers (not shown). The outer border of the photobioreactor contains microscopic hydrophobic pores, which restrict the excess pressure created by the formation of oxygen. The portion of these pores in the area of the outer border is sufficiently small to ensure that the gas flux out of the photobioreactor is realized mainly as viscous gas flow.

FIG. 2 shows a photobioreactor as cross section with a photosynthesis layer 2, where the suspension of the photoautotrophic microorganisms and a fine dispersed gaseous phase are localized in the capillary spaces of an elastic foam sheet. The gas-tight outer border of the photobioreactor is a bag consisting of a translucent relatively thick and gas-tight elastic film. Within the bag there is situated a PVC board and a planar sheet of hydrophilic, partly open-porous polyurethane foam 7. In the capillary spaces of this sheet the suspension of the photoautotrophic microorganisms is localized together with included gas in approximately equal volume portions. A PVC pipe serves as convective gas outlet channel leading to a position below the water table. The stock of photosynthesis substrate in the kind of a high concentration of hydrogen carbonate and carbonate ions is localized in the photosynthesis medium.

FIG. 3 shows a photobioreactor in the top view and a perspective view. The photobioreactor is provided with bag-shaped substrate permeable membranes and light-reflecting as well as translucent profile sheets, which control the thickness of the photosynthesis layers 2. The figure shows the arrangement of two bag-shaped membranes separating two cell-free carbon storage media from three photosynthesis layers 2 with the suspension of the photoautotrophic microorganisms. One of the carbon-storage media 4a has the same composition as the photosynthesis medium in the photosynthesis layer. The substrate-permeable membrane 3a joined to this medium consists of hydrophilic porous Nylon® with a mesh of 1 µm. The other cell-free medium 4b is a buffer containing potassium bicarbonate and potassium carbonate with a total carbon concentration of 3 mol L$^{-1}$. The substrate permeable membrane 3b joint to this medium consists of polypropylene and has a thickness of 15 µm. Both membrane bags contain a compressed profile sheet consisting of acryl glass with a wave-shaped profile. The light arriving aslope from above is reflected at the profile sheet and the gas blebs sticking to the membrane surfaces, thus ensuring a good light distribution to the depth of the space within the photobioreactor. The three photosynthesis layers 2 are interconnected for common flow. There is an elastic membrane area (not shown) in the outer wall of the photobioreactor. It is possible to create oscillating vertical flow in the photosynthesis layers by the help of vibrator acting on this membrane area.

Figure 4:
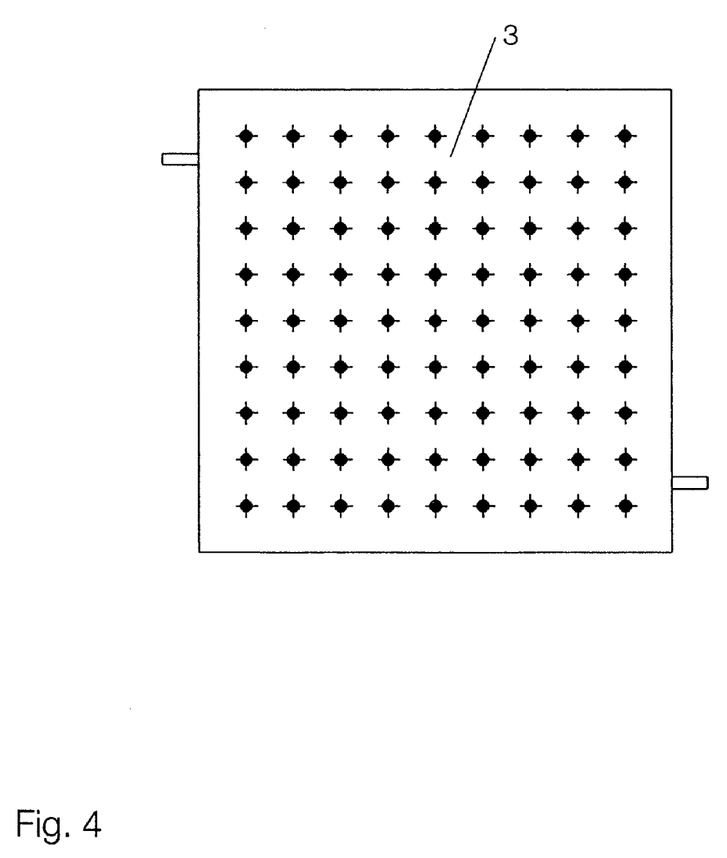

FIG. 4 shows a substrate-permeable membrane 3 arranged in parallel sheets with point-shaped agglutinations. A thin gas-permeable polypropylene membrane serves as substrate permeable membrane. Such a membrane system can be stressed and form-stabilized by the excess pressure of carbon dioxide created by the carbon storage medium and may be applied in an upright position as compartment for delivery of carbon dioxide and may control the thickness of a photosynthesis layer.

Figure 5:
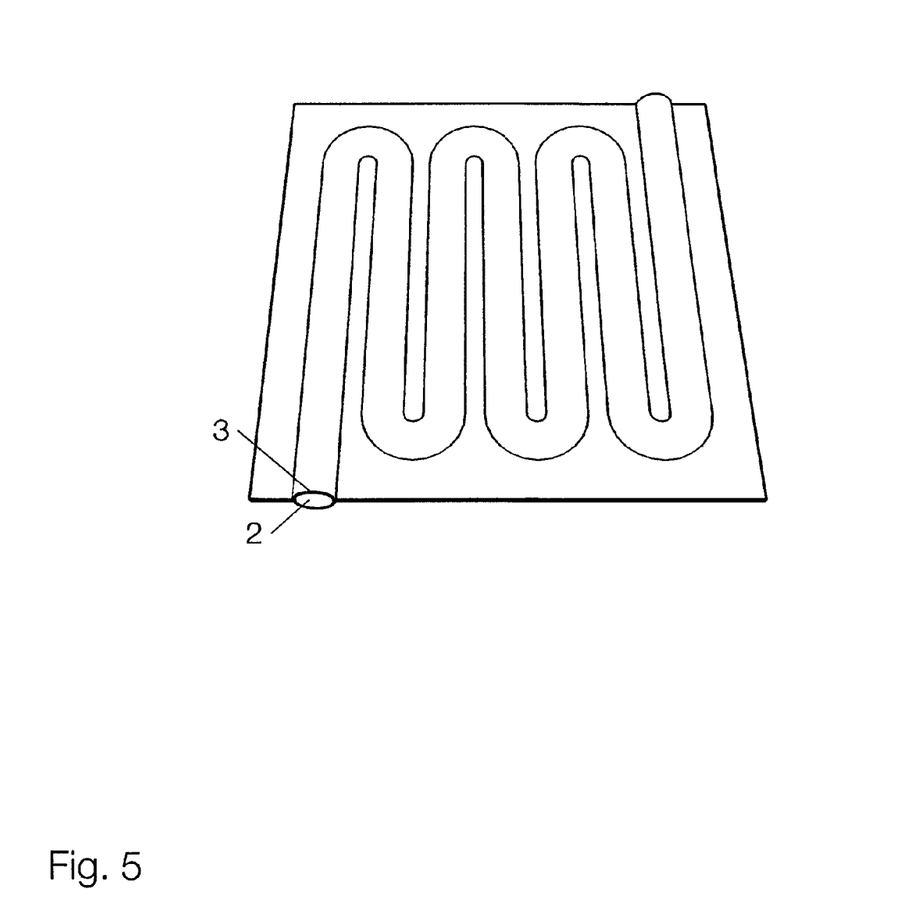

FIG. 5 shows schematically a meandering flow channel formed by a strip-shaped agglutination of two substrate-permeable membranes 3. Such membrane-bordered channels may be applied beneficially for the laminar flow of a carbon storage medium or of a photosynthesis layer.

Figure 6:
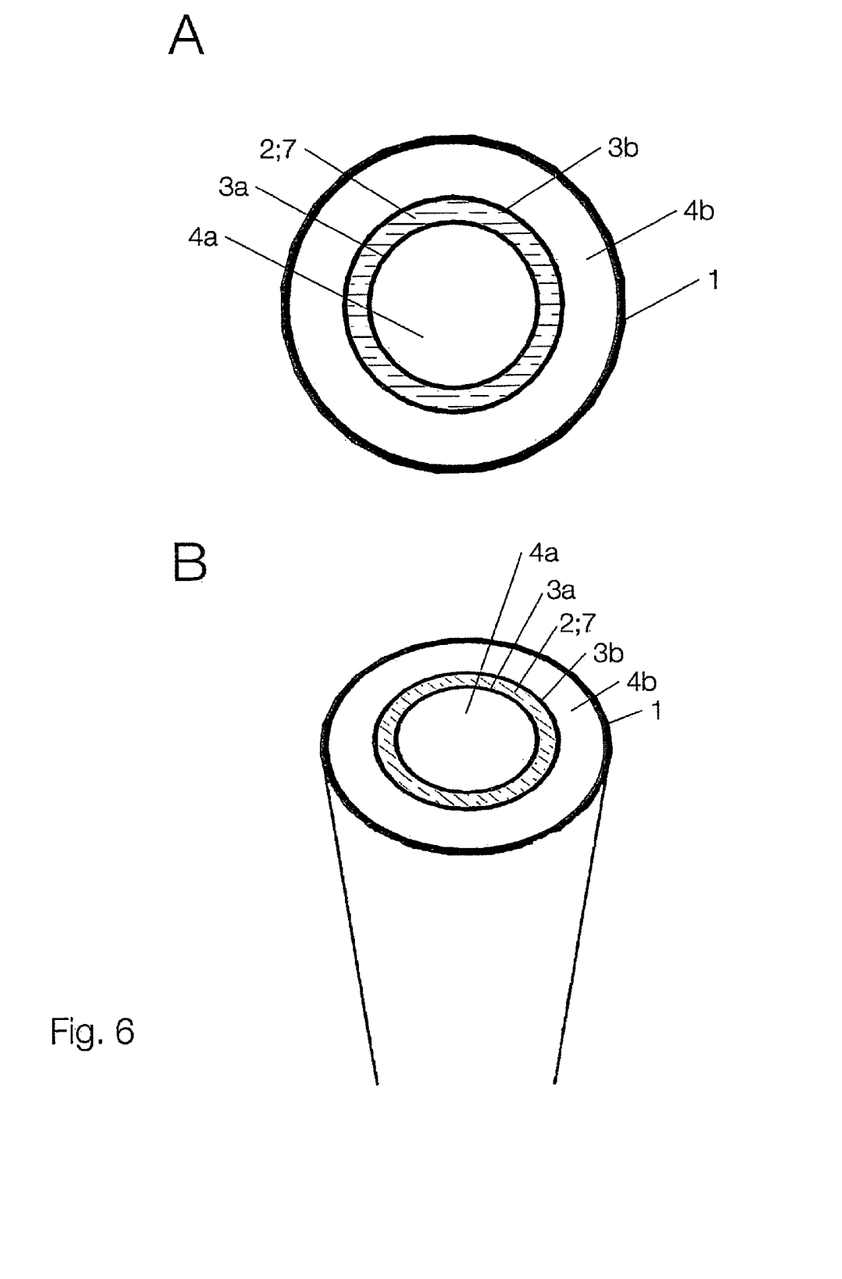
FIG. 6 the concentric arrangement of a photosynthesis layer and two membrane bordered storage media.

In the embodiment presented in FIG. 6 a concentric arrangement of a photosynthesis layer 2 and of two different carbohydrate storage media 4a and 4b is shown in a top view A and a perspective view B. The carbohydrate storage media 4a and 4b are situated at the inner face and at the outer face of the photosynthesis layer 2 and are separated from the latter by the substrate permeable membranes 3a and 3b. The photosynthesis layer 2 is bound to an elastic polyurethane foam sheet 7. The central carbohydrate storage medium 4a is a potassium bicarbonate/carbonate buffer with an initial total concentration of inorganic carbon amounting to 3 mol L$^{-1}$ and an initial carbon dioxide partial pressure of 3.2 kPa. This medium fills a tube which is formed by a thin gas-permeable polypropylene- or polyethylene membrane. It is closed hermetically on top by a translucent stopper. A weak excess pressure within the tubing established by saturation of the gas phase with carbon dioxide stabilizes the cylindrical shape of the tube. The peripheral second carbon storage medium 4b exchanges ions with the photosynthesis layer across a hydrophilic porous membrane 3b. Regarding its nutrient composition the medium 4b is consistent with the photosynthesis medium.

Figure 7:
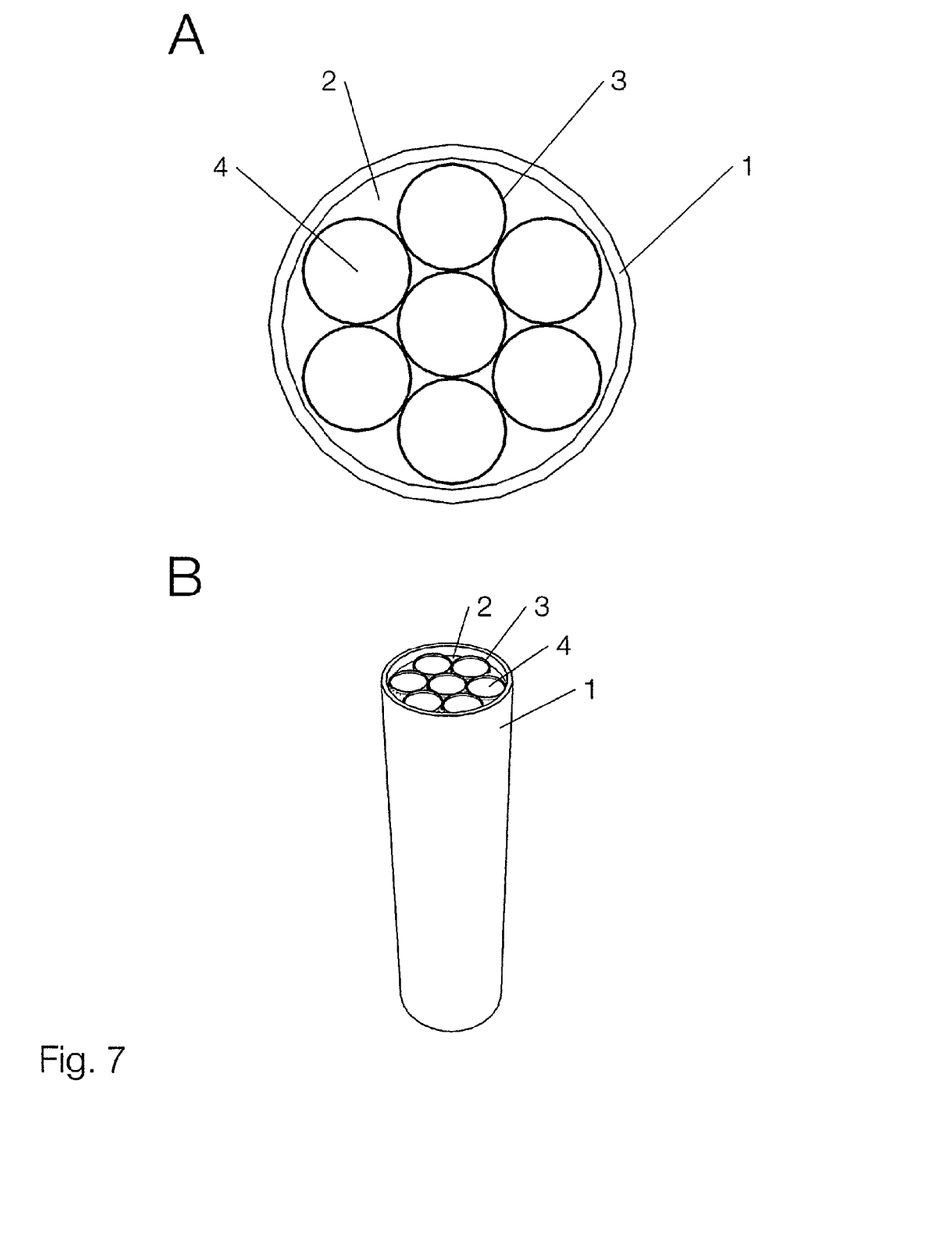
FIG. 7 an embodiment of the photobioreactor with diverse upright photosynthesis layers between membrane coated carbon storage media.

FIG. 7 shows an embodiment of a photobioreactor for the proposed process with a cylindrical gas tight outer border 1 with diverse upright photosynthesis layers 2 that are interconnected for common flow and localized between the tubular membranes filled with liquid carbon storage medium 4. It is presented in the top view in FIG. 7A and in a perspective lateral view in FIG. 7B. The carbon storage medium is a bicarbonate/carbonate buffer with a concentration of 3 mol L$^{-1}$ and a primary carbon dioxide partial pressure of 3.2 kPa. The carbohydrate storage medium fills the tubes made from a thin gas-permeable polyethylene- or polypropylene membrane. The latter are closed on top by a light transparent lock made from acryl glass. The photobioreactor comprises a gas space arranged on top of the photosynthesis layers. This gas space is connected with the atmosphere in the kind of a capillary tube made from polypropylene.

EXECUTION EXAMPLES

Example 1

In this example the culture of the cyanobacterium *Synechocystis* sp. PCC 6803 in a 4 mm thick photosynthesis layer is described. The essential components of the applied simple photobioreactor can be learned from FIG. 1A. The photobioreactor is a sterile tissue culture vessel made from acryl glass with an inner volume of 500 ml and a basic area of 200 cm$^2$, into which a volume 50 ml of a suspension of the cyanobacterium *Synechocystis* sp. PCC 6803 in a photosynthesis medium has been poured. This way a 4 mm thick photosynthesis layer with an initial biomass concentration of 0.3 g dry weight per liter was established. The photosynthesis medium contained the components of a mineral standard medium for the culture of cyanobacteria (BG-11—medium according to Schlösser, U. G (1994) Bot. Acta 107, 178 pp. It contained additionally sodium hydrogen phosphate (1 mM) for avoiding phosphate deficiency and potassium bicarbonate (200 mM) serving as carbon source for the photosynthesis during the culture period. The aslope inlet tube of the vessel (not shown) was locked by a pierced silicone rubber stopper. Elastic silicone rubber tubing with an inner diameter of 1 mm was fed through the silicone rubber stopper. This tube was led into water which served as a gas diffusion barrier between the gas space of the photobioreactor and the atmosphere. At the same time it allowed for gas release in the kind of bubbles. The photobioreactor thus described was exposed in a phytotron to continuous light with a photon flux density of 60 $\mu$mol m$^{-2}$ s$^{-1}$. 30 ml of the suspension were daily removed from the suspension and replaced by 30 ml of the fresh carbon storage medium. In the course of one weak the biomass concentration measured before the daily dilution increased to a value of 0.5 to 0.6 g dry weight per liter. This shows that the culture maintained a specific growth rate far above 1 d$^{-1}$.

Example 2

The photobioreactor used in this example had a horizontally extended photosynthesis layer and a gas outlet, wherein the photosynthesis layer was realized as three-phase system with a fine dispersed gaseous phase. FIG. 2 shows the cross section through the photobioreactor in the position of the gas outlet. A board consisting of polyvinylchloride (PVC), eight mm thick, 50 mm wide and 200 mm long, was covered by an equally sized four mm thick sheet consisting of transparent hydrophilic elastic and partially open-pored polyurethane foam. The latter was fixed with silicone to the PVC board. In the centre of the board and the polyurethane sheet there was a bore with a diameter of 5 mm. In the position of the bore through the PVC board there was a circular opening with a diameter of 4 m in the polyurethane sheet. To complete the photobioreactor, the plate with the foam sheet was introduced into a fitting membrane bag. The bag consisted of a largely gas-tight light-transparent flexible membrane made from silicone with a thickness of 0.3 mm. A fitting tube was fed through the bore in the board and polyurethane sheet and an opening of the silicone bag. The latter was glued tightly with silicone to the covering bag. The silicone bag with its content was closed with a clamp and sterilized by autoclaving. Thirty ml of a suspension of the cyanobacterium *Synechocystis* sp. PCC 6803 with a dry weight concentration of 0.1 g per liter were poured into the bag with the help of a syringe. This suspension was distributed on the foam sheet by slight pressure application to the silicone membrane. The applied photosynthesis medium had the composition described in FIG. 1. The photobioreactor thus obtained was laid on a water table. Using continuous light with a quantum flux density of 80 $\mu$mol m$^{-2}$ d$^{-1}$ an a mean biomass density of 0.8 g dry weight per liter a mean specific growth rate of 0.8 d$^{-1}$ was reached. The described photobioreactor was suitable for a semi-continuous biomass production. For harvesting of the biomass the gas outlet was taken out the bag closed by a stopper. After removal of the clamp half of the suspension was pressed off and replaced by fresh medium. This kind of harvest was carried out in 2 day intervals. After some cycles the biomass concentration at harvest time was increased to a value of 1 to 2 g dry weight per liter.

Example 3

The example explains an embodiment of the proposed photobioreactor with a rigid outer border, in which a horizontal photosynthesis layer is bordered by a gas-permeable hydrophobic membrane consisting of polyethylene and provided with carbon dioxide from a carbon storage medium by diffusion through this membrane. A meandering flow channel on the area of a bag was realized by strip-shaped thermal welding of the opposing membranes consisting of 20 $\mu$m thick polyethylene as shown in FIG. 5. Conical fittings were provided at both ends of the flow channel. The latter could be closed by inserting conical stoppers. The flow channel was filled with a suspension of cyanobacteria (0.3 g dry weight per liter) as described in FIG. 1. The membrane bordered photosynthesis layer thus formed was laid on a flat dish containing a cell-free toxic carbon storage medium realized by mixing a 3 molar solution of potassium bicarbonate with a 3 molar solution of potassium carbonate (4:1, v/v). The dish was covered by a bored lid, which had been lubricated at the border to obtain a largely gas tight cover. A hollow needle made from steel was glued into the bore to enable a largely convective gas outlet. The dish was continuously exposed to fluorescence light with an intensity of 60 $\mu$mol m$^{-2}$s$^{-1}$ (photon flux). Oxygen bubbles were formed in the photosynthesis layer by which the light was additionally scattered. The suspension in the photosynthesis layer reached a biomass concentration of ca. 5 g dry weight per liter already after three to four days.

Example 4

A photobioreactor envisaged schematically in FIG. 6 was applied. It contained a photosynthesis layer, which was in exchange with two different carbon storage media across substrate permeable membranes. The carbohydrate storage media and the photosynthesis layer were arranged concentrically as shown in FIG. 6. A dialysis tube consisting of regenerated cellulose (Union Carbide, Chicago, USA with a length of 25 mm and a diameter of 31 mm in the imbibed state was closed a the lower end and allowed to swell in water. An adapted cut of an elastic open-pored and hydrophilic polyurethane foam sheet with a thickness of 6 mm was inserted into the dialysis tube. The polyurethane foam sheet covered the inner face of the dialysis membrane up to a height of 17 cm. A culture of the cyanobacterium *Synechocystis* sp. PCC 6803 was diluted with this medium to a biomass concentration of 1 g dry weight per liter. A volume of 80 ml of the obtained suspension of this cyanobacterium was added to the foam sheet between the polyethylene membrane and the dialysis membrane. The suspension was absorbed by the foam sheet, thus forming a three-phase system with fine dispersed gaseous phase. A polyethylene film-tube with a film thickness of 50 $\mu$m and a diameter of 19 mm and a length of 25 cm was closed at the lower end, filled with a carbon storage medium which was a potassium bicarbonate solution in the toxic concentration of 3 mol $L^{-1}$ and then closed at the upper end with a light-transparent acryl glass stopper. The closed film-tube was inserted into the dialysis tube with the photosynthesis layer. The produced concentric arrangement of tubing membranes was inserted into an adapted cylindrical glass vessel. A photosynthesis medium identical with that described in example 1 was poured into the gap between the vessel wall and the dialysis tube up to a height of 19 cm. The dialysis tubing remained open on top and reached into the gas volume below the lid of the cylindrical vessel. The lid was pressed to the rubber ring on the vessel by a clamp. A 200 mm long capillary tube with an inner diameter of 0.2 mm was fed through the lid. The photosynthesis layer was exchanging bicarbonate and carbonate with the non-toxic first carbon storage medium across the dialysis membrane and was supplied moreover by the polyethylene film with carbon dioxide by the first carbon storage medium. The photobioreactor thus built was set on a light reflecting basis and exposed daily for 16 hours to the light of fluorescence lamps with a quantum flux density of 80 $\mu mol\ m^{-2}s^{-1}$. Already after one day there was a strong increase in the pigment concentration in the polyurethane sheet. The oxygen concentration within the physiological carbon storage medium raised to more the 300% of the value obtained at saturation with air. The high content of fine gas bubbles in the photosynthesis layer and the high concentration of bicarbonate ions caused a rapid exchange of carbon dioxide and oxygen between this layer and the carbon storage media. The storage of the mentioned gases within the carbon storage media prevented anaerobic conditions during the night and carbon dioxide limitation at daytime. After 12 days the cell suspension pressed off from the foam sheet had a biomass concentration of 10 to 12 g dry weight per liter. The photosynthesis layer remained vital in the course of at least four weeks and formed oxygen with high rate during the day, which resulted in a rapid increase in the oxygen concentration in the cell-free bicarbonate medium at the beginning of the light phase.

Example 5

The example regards to a variant of the proposed photobioreactor with several upright photosynthesis layers. The latter are situated between polyethylene film tubes with thin tube membrane containing the carbon storage medium in an upright arrangement as shown in FIG. 7. Cell sedimentation within the photosynthesis layer was prevented by oscillating flow. The applied photobioreactor had seven cylindrical polyethylene tubes closed below and filled with a mixture of 3 M carbon bicarbonate and 3 M potassium carbonate (v/v=4/1) that were gas-permeable and translucent (film-tubing of the Haaga GmbH, Heringsdorf, Germany) film thickness 20 μm, diameter 19 mm, length 20 mm) and were closed with an adapted acryl glass stopper. The tubing's were placed in dense packing in an adapted cylindrical glass vessel on a polypropylene grid fixed 1 cm above ground. Photosynthesis layers were built between these tubes by pouring a suspension of the green alga *Pseudockirchneriella subcapitata* in the photosynthesis medium into the gaps. The applied photosynthesis medium was a mineral medium according Kuhl and Lorenzen described by Presccott, D M (Ed.): Methods in cell Physiology, Academic Press, New York (1964) pp. 152-187 containing additionally 30 mM sodium bicarbonate. Below the grid a closed bag consisting of thin elastic silicone rubber and filled with air was situated. This bag was tightly connected with a 10 ml glass syringe by a silicone tube fed through a bore through the glass wall of the vessel. By the help of a pumping device the piston of the syringe created oscillations of the gas pressure with a frequency 10 $min^{-1}$. This way an oscillating vertical flow in the upright photosynthesis layers between the membrane tubes was created. The potassium bicarbonate buffer (3 mol $L^{-1}$) applied as carbon storage medium within the polyethylene tubes had an initial carbon dioxide partial pressure of 3.2 kPa. The vessel was supplied with a tightly closing lid and a gas outlet as described in example 5 and exposed to the light of fluorescence lamps for plant growth in a phytotron with intensity (photo flux) of 120 $\mu mol\ m^{-2}s^{-1}$. The biomass concentration at the beginning of the culture was 0.5 g dry weight per liter. After four days it amounted to about 3 g per liter. Later on, the growth rate was reduced markedly due to light limitation. In control experiments with shaken cultures, where the carbon deficiency was prevented by a membrane bordered carbon dioxide reservoir according to DE 102008029169 A1, the biomass concentration reached at the same time and the same exposure to the light was only about 1.2 g dry weight per liter. The higher growth rate in the photobioreactor described here can be explained by the better light distribution due to reflection by the upright membrane tubes and a markedly lower layer thickness. The delivery of scattered light to the photosynthesis layer was favored by the fact that there were small gas bubbles adhering at the upright polyethylene membrane.

LIST OF REFERENCE NUMERALS

1 outer border of the closed inclusion space acting as diffusion barrier
2 photosynthesis layer
3 membrane, permeable for a carbon substrate
4 carbon storage medium
5 convective gas outlet
6 spacer
7 polyurethane foam sheet

REFERENCE LIST

Eriksen N T, Biotechnol. Letters 30, 1526-1536;
Manjunath R, Geeta G S, Karnataka J. Agric. Sci. 18, 1007-1012, 2005;
Kang et al. 2009, Fresenius Environmental Bulletin 18, 687-693

The invention claimed is:
1. A method for the cultivation of photoautotrophic microorganisms for production of a biomass comprising:
Providing a closed space with an outer border (1) acting as a barrier for gas diffusion comprising at least one first compartment enclosing a photosynthesis layer (2) with a mean thickness of not more than 10 mm that contains a photosynthesis medium and photoautotrophic microorganisms suspended therein and at least one second compartment enclosing a cell-free carbon storage medium (4) that is separated from the first compartment by a porous hydrophilic membrane (3) and is transparent to light;
Exposing the photosynthesis layer (2) to light without whirling a gas within the photosynthesis medium or piping a gas through the photosynthesis medium;
Maintaining a bicarbonate concentration of at least 10 mM in the photosynthesis layer by diffusion of bicarbonate through the porous hydrophilic membrane from the cell-free carbon storage medium; and
Convective channeling away of the gas volume formed by photosynthesis through an appliance for a gas outlet that restricts diffusive gaseous exchange, wherein the photoautotrophic microorganisms form a biomass.

2. The method of claim 1, wherein the bicarbonate concentration is maintained by diffusion from the carbon storage medium through the porous hydrophilic membrane that is permeable to bicarbonate ions and all other mineral nutrients using a photobioreactor exhibiting at least one first compartment enclosing the photosynthesis layer and at least one second compartment enclosing a carbon storage medium that is separated from the first compartment by the porous hydrophilic membrane and contains bicarbonate ions with an initial concentration above 50 mM, as well as all further inorganic constituents of the photosynthesis medium.

3. The method of claim 2, wherein
either the cell suspension of the photosynthesis layer or the cell free storage medium separated from the photosynthesis layer by the porous hydrophilic membrane or both are continuously or discontinuously flowing through their compartment.

4. The method of claim 2, wherein
carbon dioxide is delivered from a first carbon storage medium to a second carbon storage medium through a gas-permeable hydrophobic membrane and bicarbonate ions are delivered to the photosynthesis layer (2) through a translucent hydrophilic porous membrane.

5. The method of claim 1, wherein
the bicarbonate concentration is maintained by diffusion of carbon dioxide from a carbon storage medium through a gas-permeable hydrophobic membrane using a photobioreactor exhibiting at least one first compartment enclosing the photosynthesis layer (2) and at least one second compartment enclosing a carbon storage medium (4) that is separated from the first compartment by a gas-permeable hydrophobic membrane, that is impermeable to liquid water,
carbon dioxide is reversibly bound in a chemical or physical manner to the carbon storage medium, the latter containing a solid material, an aqueous solution or an organic liquid reversibly binding carbon dioxide as known for ion exchange resins, solutions of bicarbonates, carbonates, carbamates as well as for solutions of carbon dioxide in organic solvents, and
the concentration of bound carbon dioxide in the cell-free carbon storage medium is above 1 mol $L^{-1}$.

6. The method of claim 1, wherein
at least one compartment is a bag built from a translucent substrate-permeable membrane and
the distance between opposed membrane areas of a bag or between neighboring bags are fixed by at least one spacer consisting of a translucent and/or light-reflecting material.

7. The method of claim 6, wherein said spacer has a folded or wave-shaped elastically compressed profile.

8. The method of claim 7, wherein a sheet consisting of foamed elastomer like polyurethane or latex is applied as the space filling open-pored light transparent solid material.

9. The method of claim 8, wherein the biomass is separated from the foam sheet by pressing or sucking of a liquid phase from the three-phase system using a press, a roller or a suction pump.

10. The method of claim 1 wherein the photosynthesis layer is absorbed within a translucent space-filling open-pored solid material which creates a three-phase system with a stable fine-disperse gas phase by capillary absorption of an aqueous liquid.

* * * * *